(12) United States Patent
Ball et al.

(10) Patent No.: US 6,860,888 B2
(45) Date of Patent: Mar. 1, 2005

(54) CUTTING DEVICE FOR USE IN A MEDICAL PROCEDURE

(75) Inventors: Robert Ball, Winona Lake, IN (US); Carl Basamania, Chapel Hill, NC (US)

(73) Assignee: DePuy Orthopaedics, Inc., Warsaw, IN (US)

( * ) Notice: Subject to any disclaimer, the term of this patent is extended or adjusted under 35 U.S.C. 154(b) by 360 days.

(21) Appl. No.: 10/074,372

(22) Filed: Feb. 11, 2002

(65) Prior Publication Data

US 2003/0163151 A1 Aug. 28, 2003

(51) Int. Cl.[7] .......................... A61B 17/88; A61B 17/32; B26D 1/00
(52) U.S. Cl. ......................... 606/104; 606/79; 606/167; 606/174; 83/199; 83/200
(58) Field of Search .................. 606/167, 170, 606/174, 79–85; 30/95, 97, 110; 83/196–200; 82/57, 58, 73

(56) References Cited

U.S. PATENT DOCUMENTS

| 853,832 | A | * | 5/1907 | Ryan ........................... 30/240 |
| 2,894,324 | A | * | 7/1959 | Hardin ......................... 30/240 |
| 3,315,669 | A | * | 4/1967 | Rhodes ....................... 606/101 |
| 4,051,596 | A | | 10/1977 | Hofmann |
| 4,850,354 | A | | 7/1989 | McGurk-Burleson et al. |
| 4,940,074 | A | * | 7/1990 | Menard ....................... 83/199 |
| 5,513,434 | A | | 5/1996 | Hamman |
| 6,209,207 | B1 | | 4/2001 | Patterson et al. |

FOREIGN PATENT DOCUMENTS

| RU | 1706603 A1 | 1/1992 |
| RU | 1725870 A1 | 4/1992 |

* cited by examiner

*Primary Examiner*—David O. Reip
*Assistant Examiner*—Sarah Webb
(74) *Attorney, Agent, or Firm*—Maginot, Moore & Beck

(57) ABSTRACT

A cutting device for use in a medical procedure includes a housing having a housing cavity and defining a first cutting surface. An actuator is positioned within the housing cavity and has a first cam member. A cutting member is positioned with the housing cavity and has a second cam member. The cutting member defines a second cutting surface. Movement of the actuator within the housing cavity causes the first cam member to cooperate with the second cam member so as to rotate the cutting member relative to the housing. Rotation of the cutting member relative to the housing causes the second cutting surface to move relative to the first cutting surface to effectuate a cutting operation.

31 Claims, 13 Drawing Sheets

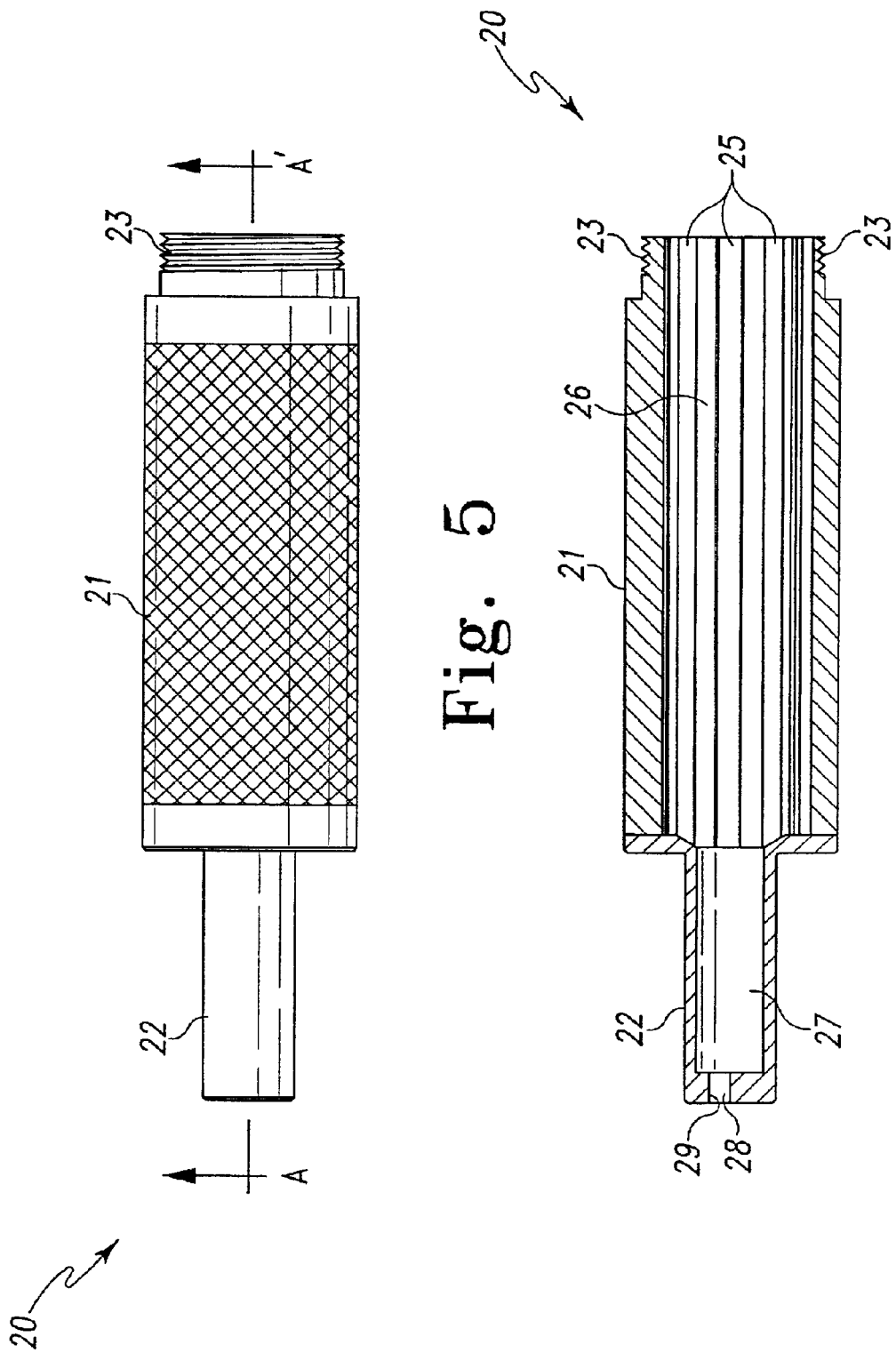

US 6,860,888 B2

CUTTING DEVICE FOR USE IN A MEDICAL PROCEDURE

FIELD OF THE INVENTION

The present invention generally relates to cutting devices that are used in medical procedures, and more particularly, to a cutting device operable to cut pins such as those used in the repair of orthopedic fractures.

BACKGROUND OF THE INVENTION

Orthopedic fractures may be repaired by a variety of techniques. According to one technique, a device such as a pin or rod may be utilized to maintain bone fragments such as a clavicle or tibia in a fixed relationship to one another. Such devices are commercially available from a number of orthopedic device manufacturers, such as DePuy Orthopedics, Inc. of Warsaw, Ind.

When using a pin to repair a fracture, a portion of the pin is typically inserted into a fractured bone, while the remaining portion of the pin extends externally from the bone and is connected to a retention member made up of a fastener such as a nut or a plurality of nuts. The retention member can then be tightened to reduce the fractured bone, thereby bringing the bone fragments back into alignment. Although such pins are typically available in a variety of different lengths, it is not uncommon for some excess portion of the pin to extend beyond the retention member after the latter is tightened. Accordingly, it is generally desirable to remove this excess portion of the pin to reduce patient discomfort and/or facilitate proper healing.

One conventional device for removing this excess portion of the pin during the above-identified medical procedure is a "bolt-cutter" type device. However, this device has several disadvantages when used during such a medical procedure. First, the "bolt cutter" type device tends to be rather large and bulky thereby causing it to be unstable and awkward to use. Further, when the "bolt cutter" device is used to remove the above-described excess pin portion, the severed pin may still extend through the retention member so as to cause a small "stub" to project outwardly from the retention member. The presence of this small stub within the subcutaneous tissue of the patient may cause aggravation and pain for the patient. Moreover, such conventional cutting device tends to leave burrs on the end of the severed pin after such cutting device is used to sever the excess pin portion. These burrs, if not removed, are a further source of irritation for the patient. However, removal of these burrs undesirably lengthens the duration of the medical procedure. Furthermore, due to the relatively large size of the "bolt cutter" type cutting device, the incision which exposes the implanted pin must be correspondingly larger in order to enable such cutting device to be advanced through such incision into operative contact with the excess pin portion. Thus, use of the "bolt type" cutting device does not readily facilitate performance of the medical procedure through a relatively small incision.

In order to avoid some of the above-identified problems, there have been attempts to cut the pin prior to insertion into a bone. However, this approach also has significant drawbacks. Indeed, if the pin is cut so as to be sized too short, the pin may have to be discarded and another pin would have to be cut and used. Alternatively, if the pin is cut so as to be sized too long, the pin may have to be cut again while it is coupled to the bone and only accessible through an incision. The drawbacks of this latter situation were identified above.

Accordingly, there is a need for a cutting device that avoids the aforementioned problems and is capable of accurately and efficiently performing a pin cutting operation during a medical procedure, such as the repair of an orthopedic fracture. The present invention addresses these and other issues.

SUMMARY OF THE INVENTION

In accordance with one embodiment of the present invention, a cutting device for use in a medical procedure includes a housing having a housing cavity and defining a first cutting surface. An actuator is positioned within the housing cavity and has a first cam member. A cutting member is positioned with the housing cavity and has a second cam member. The cutting member defines a second cutting surface. Movement of the actuator within the housing cavity causes the first cam member to cooperate with the second cam member so as to rotate the cutting member relative to the housing. Rotation of the cutting member relative to the housing causes the second cutting surface to move relative to the first cutting surface to effectuate a cutting operation.

In accordance with another embodiment of the present invention, a cutting device for use in a medical procedure includes a housing having a housing cavity and defining a first cutting surface. An actuator is positioned within the housing cavity and has a cam groove formed therein. A cutting member is positioned with the housing cavity and has a cam follower. The cutting member defines a second cutting surface. A driver is configured to move in relation to the housing. Movement of the driver in relation to the housing causes the actuator to move within the housing cavity. Movement of the actuator within the housing cavity causes the cam groove to cooperate with the cam follower so as to rotate the cutting member relative to the housing. Rotation of the cutting member relative to the housing causes the second cutting surface to move relative to the first cutting surface to effectuate a cutting operation.

In accordance with still another embodiment of the present invention, a cutting device for use in a medical procedure includes a housing having a housing cavity and defining a first cutting surface. An actuator is positioned within the housing cavity and has a cam groove defining a cam groove surface formed therein. A cutting member is positioned with the housing cavity and has at least one protrusion extending outwardly therefrom. The cutting member defines a second cutting surface. Movement of the actuator within the housing cavity causes the cam groove surface to cooperate with the at least one protrusion so as to rotate the cutting member relative to the housing. Rotation of the cutting member relative to the housing causes the second cutting surface to move relative to the first cutting surface to effectuate a cutting operation.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein:

FIG. 5 is a side elevational view of the housing of FIG. 3;

FIG. 6 is a cross-sectional side view of the housing taken along line A–A' of FIG. 5;

The exemplifications set out herein illustrate preferred embodiments of the invention, and such exemplifications are not to be construed as limiting the scope of the invention in any manner.

DESCRIPTION OF THE PREFERRED EMBODIMENTS

Figure 1:
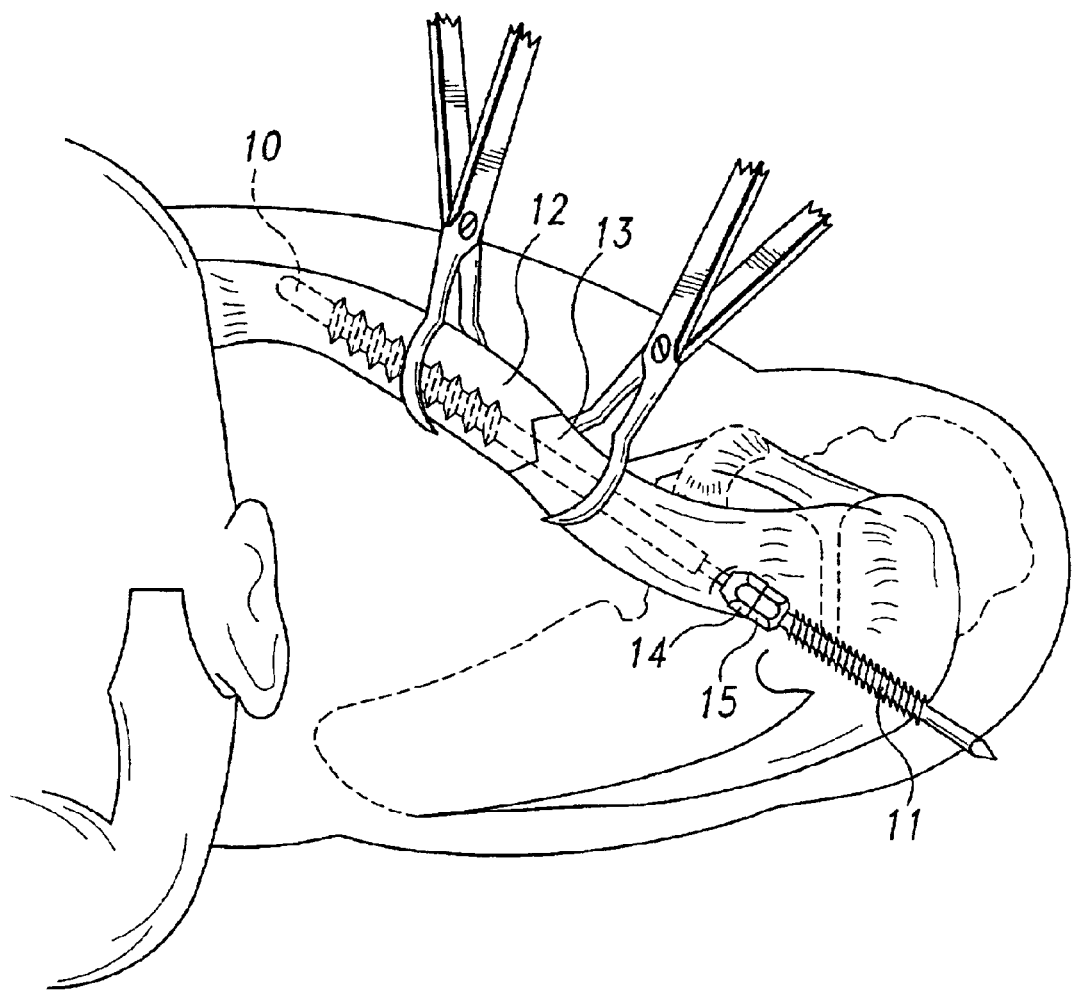
FIG. 1 is a diagram illustrating an exemplary medical procedure in which the cutting device of the present invention may be used.

Referring now to the drawings, and more particularly to FIG. 1, a diagram of an exemplary medical procedure where a cutting device of the present invention may be used is shown. For purposes of example and explanation, FIG. 1 depicts a medical procedure in which a pin is used in the repair of a clavicle fracture. It is noted, however, that the cutting device of the present invention may be used in other types of medical procedures. For example, the cutting device of the present invention may be used to perform a pin cutting operation in other types of orthopedic procedures, such as in the repair of a tibia or any other bone in the body of a patient.

As shown in FIG. 1, a portion of a pin 10 is placed within clavicle fragments 12 and 13. Retention members 14 and 15 are used to reduce the fractured bone, thereby bringing the bone fragments 12 and 13 back into alignment. Once the fractured bone is reduced, an excess portion of the pin 11 extends outwardly from the patient's body. As will be explained hereinafter, this excess portion of the pin 11 can be removed using the cutting device of the present invention.

Figure 2:
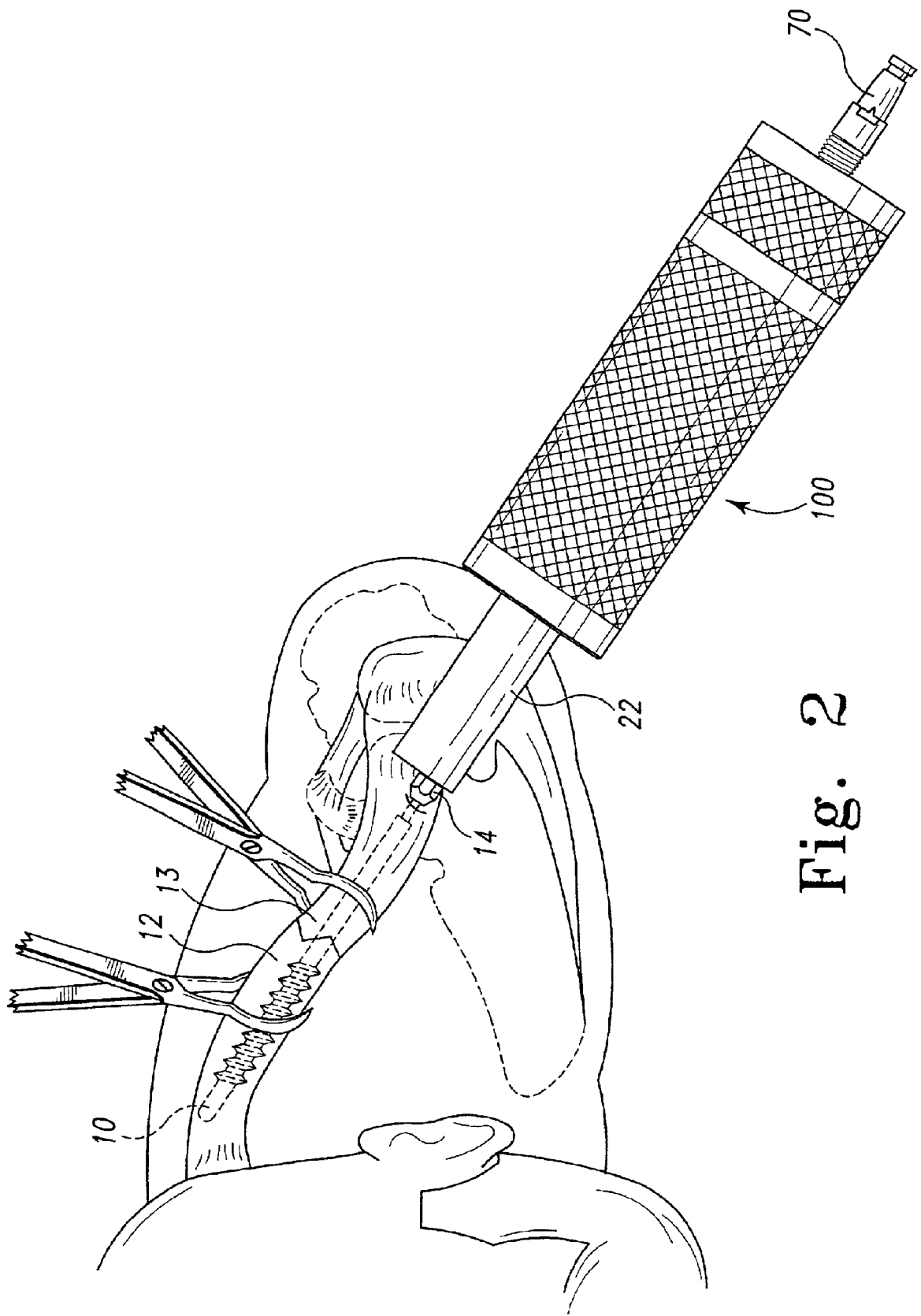
FIG. 2 is a diagram similar to FIG. 1, but showing the cutting device of the present invention being used to carry out a pin cutting operation.

FIG. 2 illustrates how the cutting device of the present invention is used to perform a pin cutting operation during the medical procedure depicted in FIG. 1. As indicated in FIG. 2, the cutting device 100 of the present invention is placed over the excess portion of the pin 11 and the retention member 15 previously shown in FIG. 1. The cutting device 100 is then manipulated to cut the excess portion of the pin 11 flush with the end of the retention member 15. According to an exemplary embodiment, the cutting device 100 may be connected to an external device such as a power drill (not shown) to effectuate the cutting operation. Further details of the cutting device 100 of the present invention will now be provided with reference to FIGS. 3 through 22.

Figure 3:
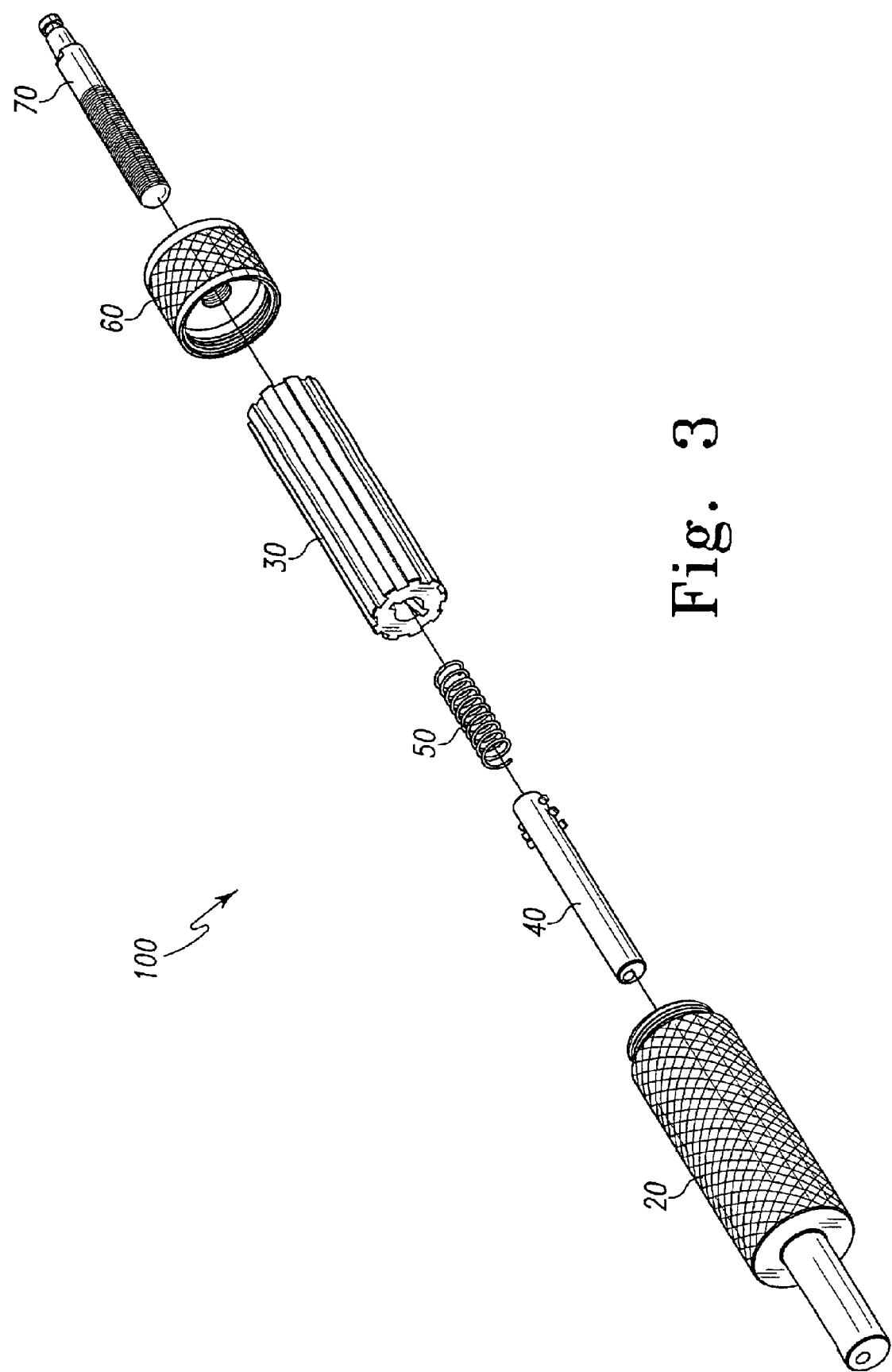
FIG. 3 is an exploded perspective view of the cutting device of FIG. 2.

Referring to FIG. 3, an exploded perspective view of the cutting device 100 is shown. As indicated in FIG. 3, the cutting device 100 includes a housing 20, an actuator 30, a cutting member 40, a spring 50, an end cap 60, and a drive shaft 70. Each of the aforementioned elements is preferably constructed of a durable metallic material, such as stainless steel or other material. Further details regarding each of these elements will hereinafter be provided.

Figure 4:
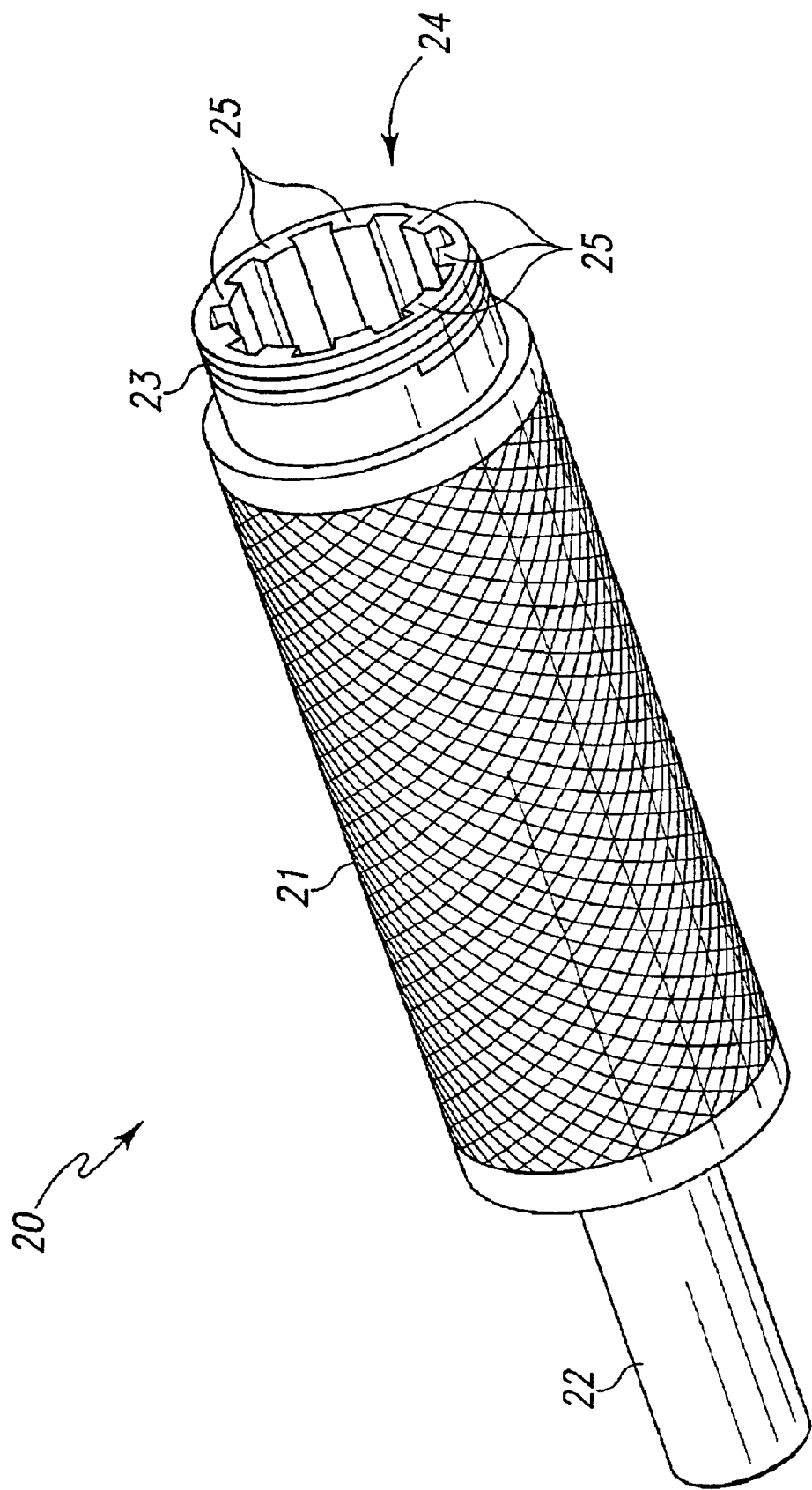
FIG. 4 is a perspective view of the housing of the cutting device of FIG. 2.
Figure 7:
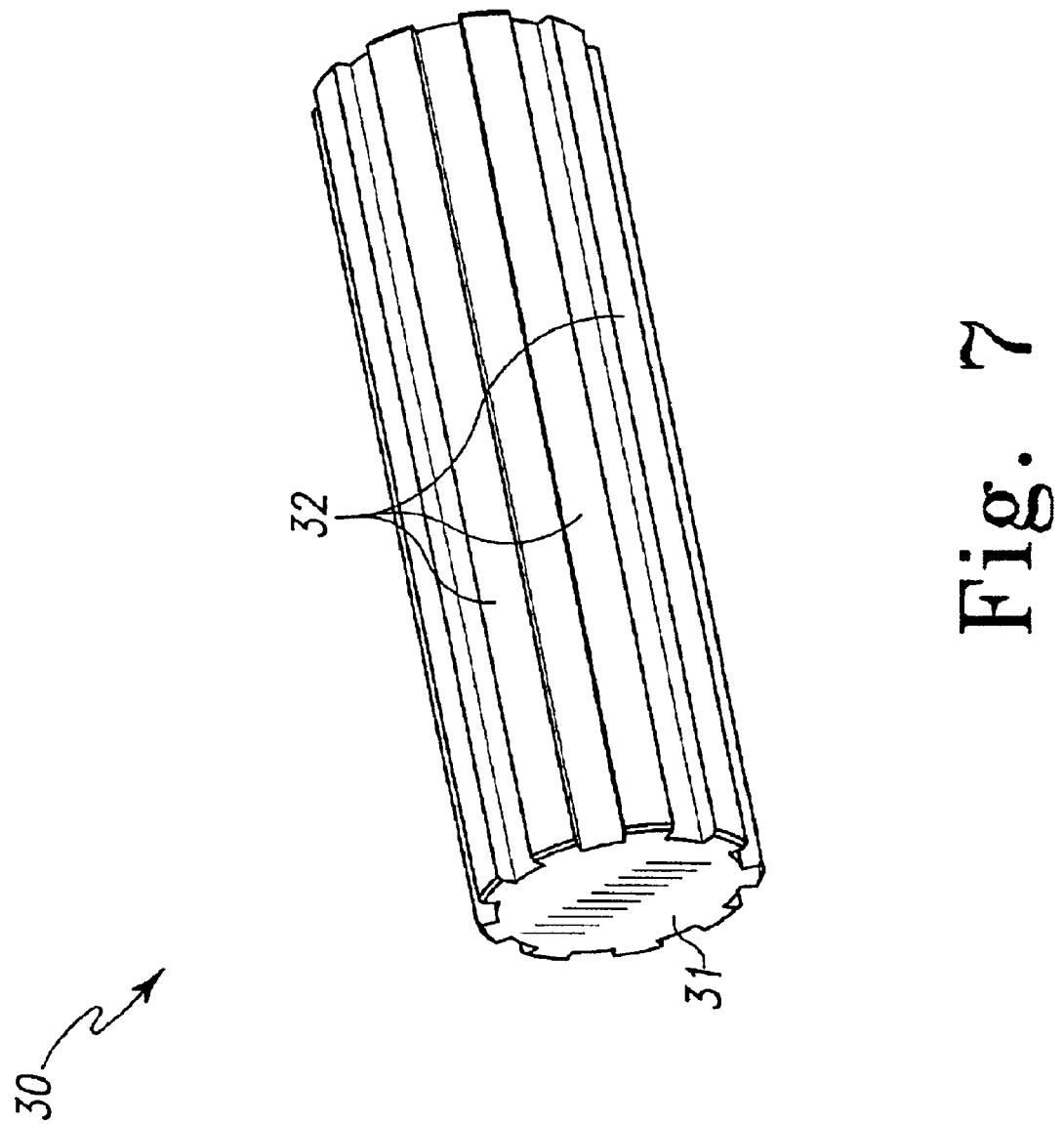
FIG. 7 is a perspective view of the actuator of the cutting device of FIG. 2.
Figure 9:
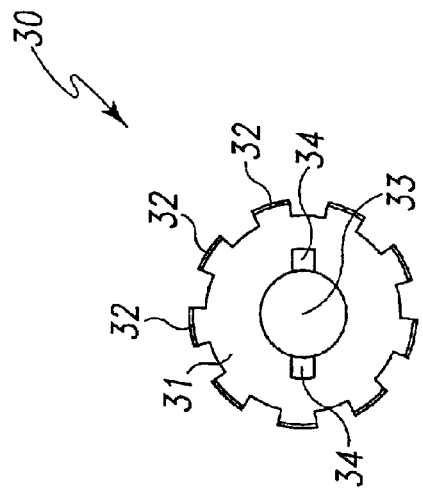
FIG. 9 is an end elevational view of the actuator of FIG. 7.
Figure 8:
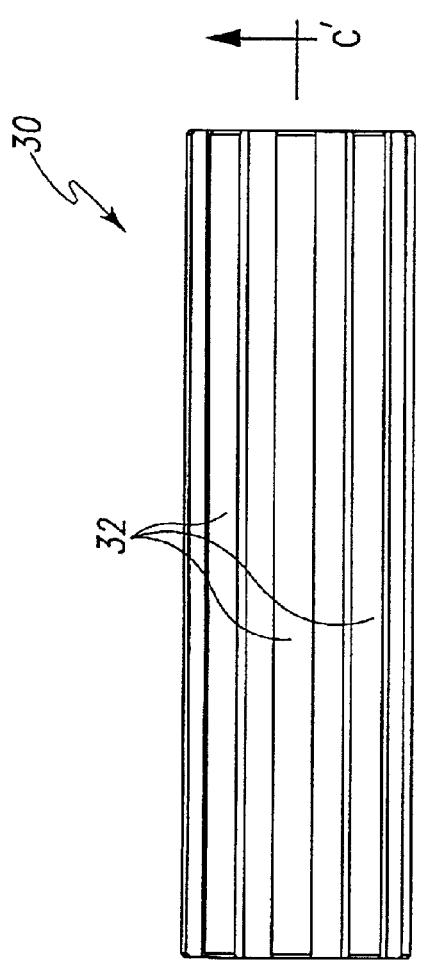
FIG. 8 is a side elevational view of the actuator of FIG. 7.
Figure 10:
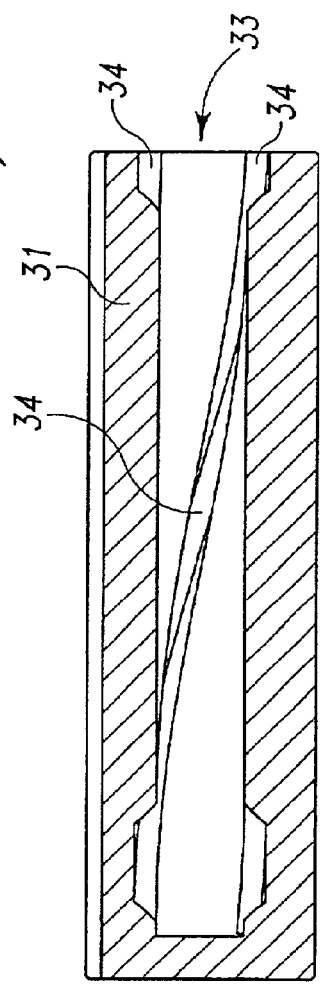
FIG. 10 is a cross-sectional view of the actuator taken along line C–C' of FIG. 8.
Figure 20:
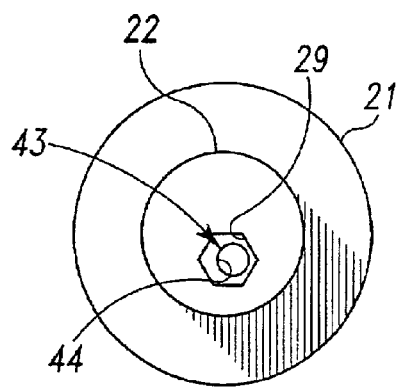
FIGS. 20 to 22 are elevational views which depict sequential movement of cutting surface 44 relative to cutting surface 29 during operation of the cutting device of FIG. 2.
Figure 21:
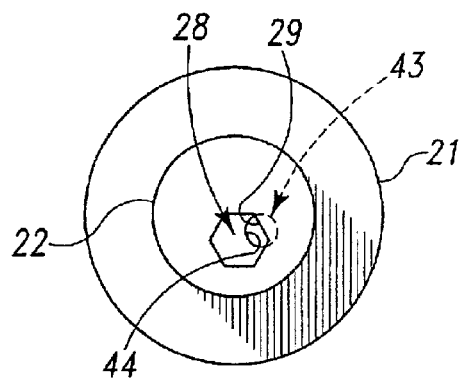
Figure 22:
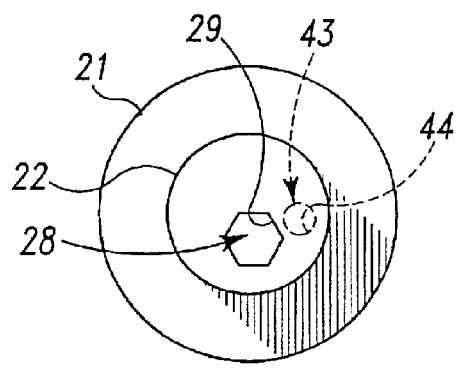

Referring to FIGS. 4 through 6, further details of the housing 20 are provided. In particular, the housing 20 includes an increased diameter portion 21 and a reduced diameter portion 22. A threaded portion 23 is formed on one end of the increased diameter portion 21. A housing cavity 24 is formed within the increased diameter portion 21 and the reduced diameter portion 22 (see also FIG. 6). In particular, the housing cavity 24 includes an increased diameter cavity 26 formed within the increased diameter portion 21, and a reduced diameter cavity 27 formed within the reduced diameter portion 22. A plurality of internal flutes 25 is formed within the increased diameter cavity 26. An opening 28 into the reduced diameter cavity 27 is formed at one end of the reduced diameter portion 22. According to an exemplary embodiment, the opening 28 is polygonal (e.g., hexagonal), as shown in FIGS. 20–22. According to another embodiment, the opening 28 may be circular. (For example, FIG. 3 shows an alternative embodiment of the opening 28 being circular.) The opening 28 may also exhibit a different shape and/or be a combination of different shapes (e.g., half circular and half hexagonal). A cutting surface 29 is defined on the reduced diameter portion 22 by the opening 28.

Referring to FIGS. 7 through 10, further details of the actuator 30 are provided. The actuator 30 is positioned within the increased diameter cavity 26 of the housing 20 when the cutting device 100 is in an assembled state. The actuator 30 includes a main body 31 having a plurality of external flutes 32 defined therein. The external flutes 32 of the actuator 30 cooperate with the internal flutes 25 of the housing 20 to facilitate axial movement of the actuator 30 within the increased diameter cavity 26 of the housing 20 during a cutting operation. An actuator cavity 33 is formed within the main body 31 of the actuator 30. At least one cam member 34 is located within the actuator cavity 33. According to an exemplary embodiment, each cam member 34 is embodied as an arcuate (e.g., helical) cam groove defining a cam surface within the actuator cavity 33. In the illustrated embodiment, two such cam members 34 are formed within the actuator cavity 33 and spaced apart from each other by 180°.

Figure 11:
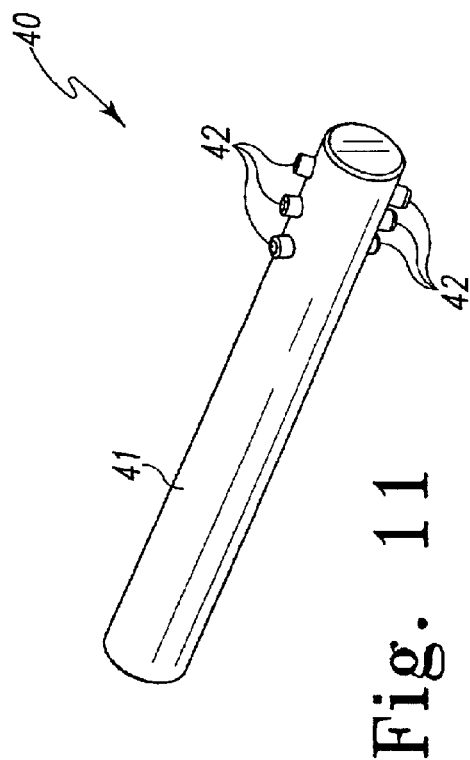
FIG. 11 is a perspective view of the cutting member of the cutting device of FIG. 2.
Figure 13:
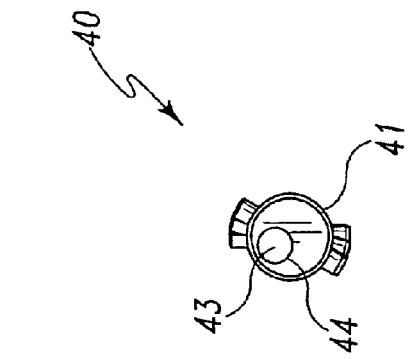
FIG. 13 is a second side elevational view of the cutting member of FIG. 11.
Figure 12:
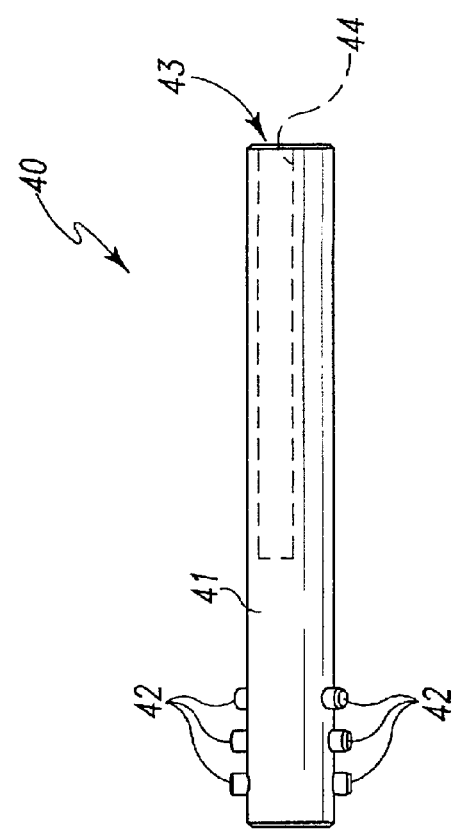
FIG. 12 is a first side elevational view of the cutting member of FIG. 11.

Referring to FIGS. 11 through 13, further details of the cutting member 40 are provided. In particular, the cutting member 40 includes a cylindrical shaft 41 and at least one cam member 42. According to an exemplary embodiment, each cam member 42 is embodied as a protrusion extending outwardly from an outer surface of the shaft 41. In the illustrated embodiment, the cutting member 40 includes six such cam members 42. In particular, the cam members 42 are arranged in two sets, and each set includes three cam members 42. According to this embodiment, each set of cam members 42 is positioned within a cam groove defined by a corresponding cam member 34 of the actuator 30 when the cutting device 100 is in an assembled state. When the actuator 30 moves axially within the increased diameter portion 26 of the housing 20, each set of cam members 42 rides within a respective cam groove defined by a corresponding cam member 34 of the actuator 30. In turn, this causes the cutting member 40 to rotate relative to the housing 20. In this manner, each of the cam members 42 of the cutting member 40 operates as a cam follower.

According to an alternative embodiment, the cam member 42 of the cutting member 40 may be embodied as one or more cam grooves, and the cam member 34 of the actuator 30 may be embodied as one or more protrusions. In this embodiment, the cam member 34 of the actuator 30 operates as a cam follower. In both embodiments, however, the cam member 34 of the actuator 30 and the cam member 42 of the cutting member 40 cooperate with one another as the actuator 30 and the cutting member 40 move relative to one another between different orientations during a cutting operation.

A shaft cavity 43 is formed within the shaft 41 of the cutting member 40. A cutting surface 44 is defined by an inner wall of the shaft cavity 43. When the cutting device 100 is in an assembled state, the cutting member 40 is positioned at least partially within the reduced diameter cavity 27 of the housing 20 so that the cutting surface 44 of the cutting member 40 is positioned adjacent to the cutting surface 29 of the housing 20. The cutting surface 44 of the cutting member 40 and the cutting surface 29 of the housing 20 are moveable in relation to one another between different orientations.

Figure 14:
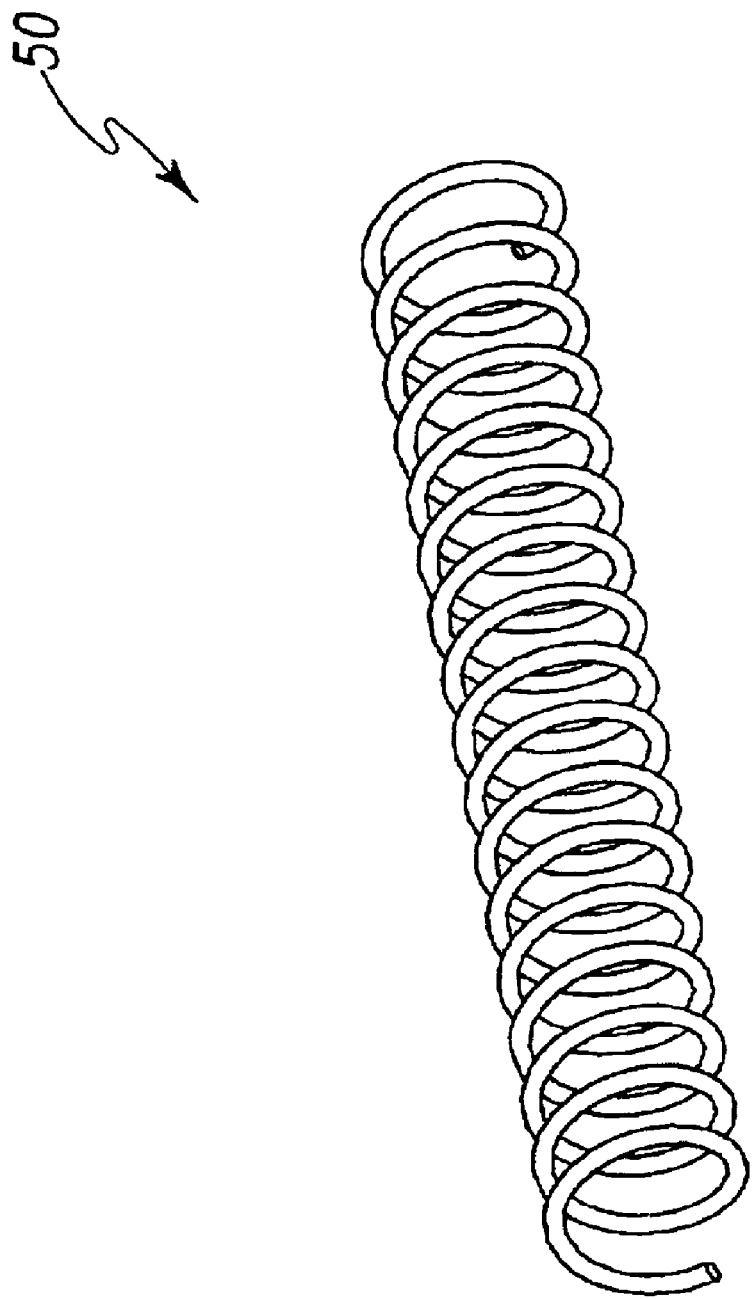
FIG. 14 is a perspective view of the spring of the cutting device of FIG. 2.
Figure 16:
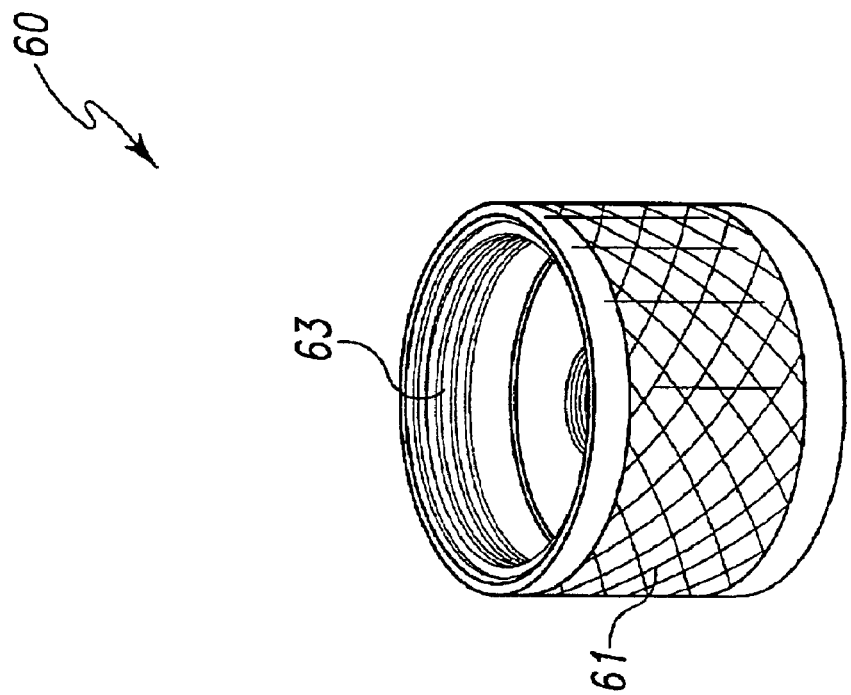
FIG. 16 is a second perspective view of the end cap of FIG. 15.
Figure 15:
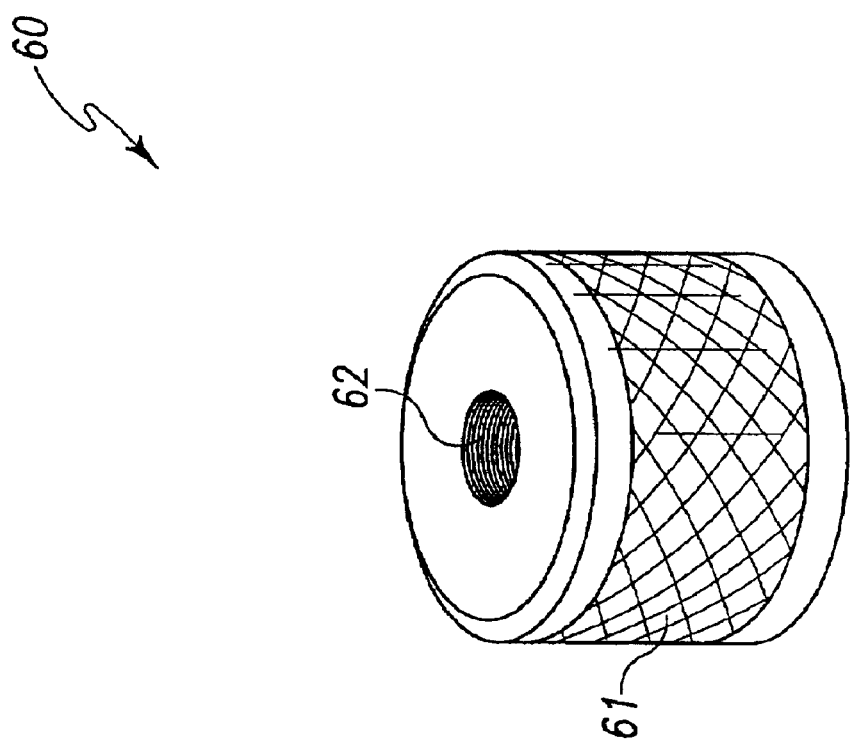
FIG. 15 is a first perspective view of the end cap of the cutting device of FIG. 2.
Figure 18:
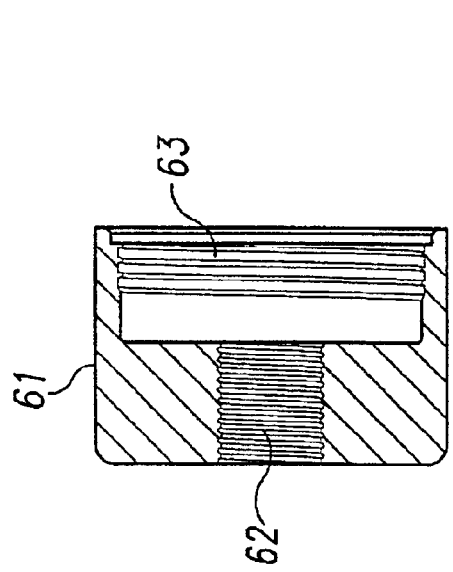
FIG. 18 is a cross-sectional view of the end cap taken along line E–E' of FIG. 17.
Figure 17:
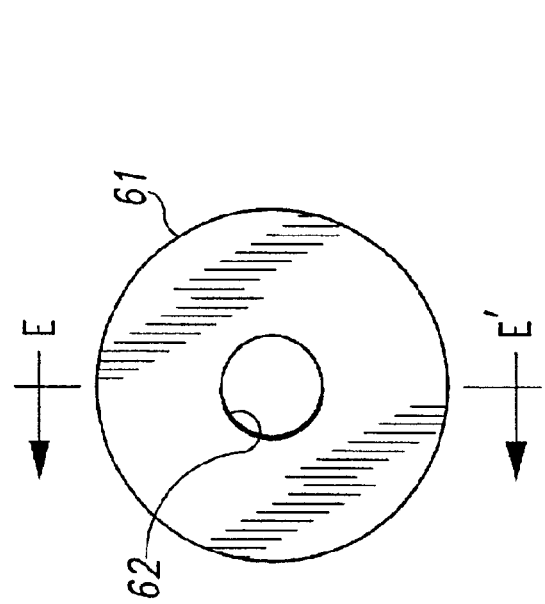
FIG. 17 is a plan view of the end cap of FIG. 15.

Referring to FIG. 14, further details of the spring 50 are provided. In particular, the spring 50 is preferably embodied as a helical, wire spring, but may be embodied as any suitable resilient member. The spring 50 is positioned within the actuator cavity 33 when the cutting device 100 is in an assembled state, and applies a bias force to the actuator 30 and the cutting member 40. According to an exemplary embodiment, the spring 50 applies a bias force such that absent other forces (i) the actuator 30 is positioned at a predetermined location within the housing cavity 24, and (ii) the cutting surface 44 of the cutting member 40 exhibits a predetermined orientation relative to the cutting surface 29 of the housing 20. Of course, the actuator 30 and the cutting member 40 become displaced from these orientations as force is applied to the actuator 30 during a cutting operation. However, as this force is removed from the actuator 30, the spring 50 biases the actuator 30 and the cutting member 40 back to their predetermined orientations. It should be appreciated that the spring 50 further functions to bias the cutting surface 44 of the cutting member 40 in close proximity to the cutting surface 29 of the housing 20 during the cutting operation.

Referring to FIGS. 15 through 18, further details of the end cap 60 are provided. In particular, the end cap 60 includes a main body 61 having a reduced diameter threaded portion 62 and an increased diameter threaded portion 63. When the cutting device 100 is in an assembled state, the increased diameter threaded portion 63 threadably engages the threaded portion 23 of the housing 20, and the reduced diameter threaded portion 62 threadably engages the drive shaft 70. As will be explained later herein, the end cap 60 and the drive shaft 70 can be used independently or together as a driver for the actuator 30. This driving action causes the actuator 30 to move axially within the housing cavity 24 when the cutting device 100 performs a cutting operation.

Figure 19:
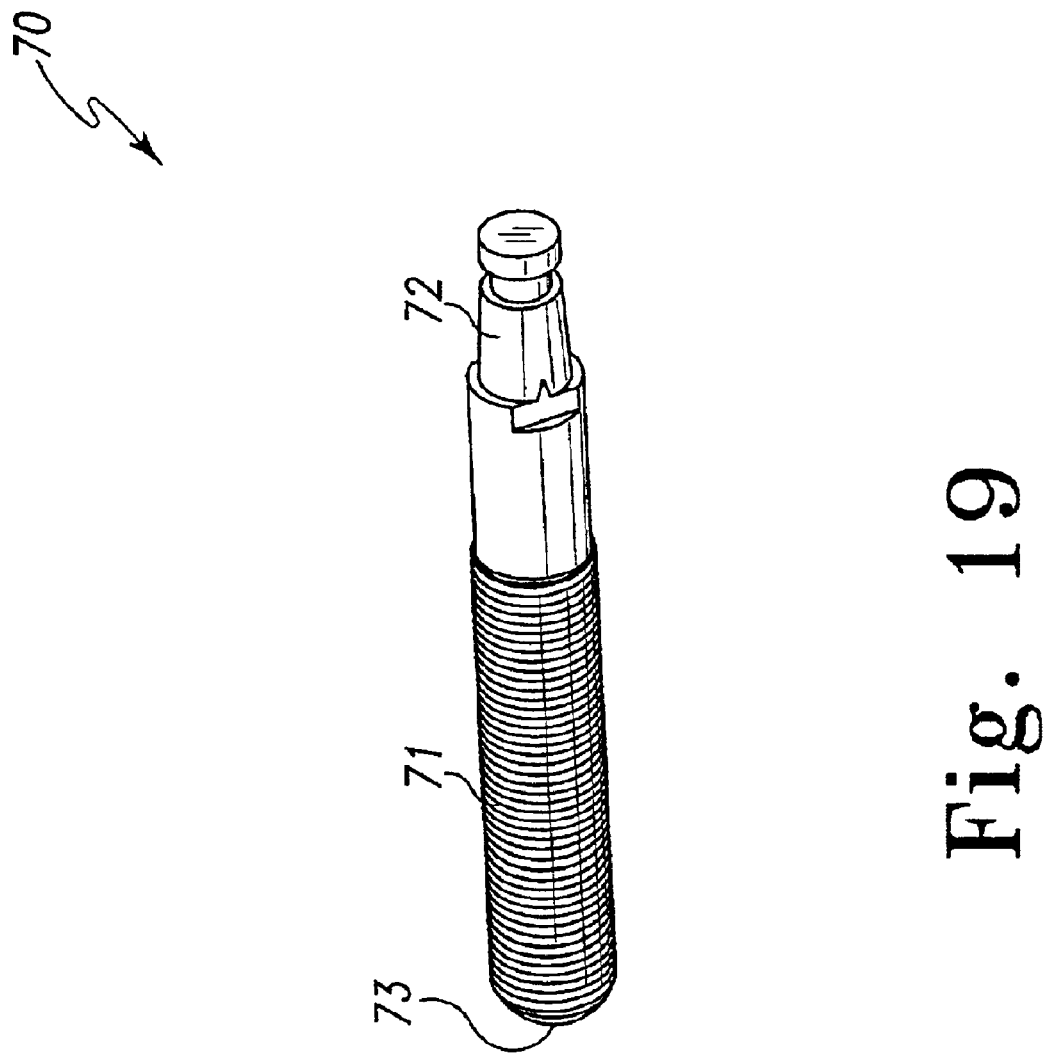
FIG. 19 is a perspective view of the drive shaft of the cutting device of FIG. 2.

Referring to FIG. 19, further details of the drive shaft 70 are provided. In particular, the drive shaft 70 includes a threaded portion 71, a connecting portion 72, and a contact portion 73. The threaded portion 71 threadably engages the reduced diameter threaded portion 62 of the end cap 60 when the cutting device 100 is in an assembled state. The connecting portion 72 is connectable to an external device, such as a power drill, and enables the drive shaft 70 to receive a rotational force therefrom. The contact portion 73 engages the main body 31 of the actuator 30, and causes the actuator 30 to move axially within the housing cavity 24 as the end cap 60 and/or the drive shaft 70 are rotated.

Operation of Cutting Device 100

Further details regarding an exemplary operation of the cutting device 100 will now be provided. To initiate a cutting operation, the cutting device 100 is first placed over the excess portion of the pin 11 and the retention member 15, as shown in FIG. 2. In particular, the excess portion of the pin 11 is inserted through the opening 28 formed in the reduced diameter portion 22 of the housing 20 until the cutting device 100 is in the position shown in FIG. 2. Prior to this insertion, however, the opening 28 and the shaft cavity 43 of the cutting member 40 should be aligned, as shown in FIG. 20. This alignment is necessary so that the excess portion of the pin 11 moves into the shaft cavity 43 as the pin 11 is inserted through the opening 28. Alignment of the opening 28 and the shaft cavity 43 can be achieved by moving the actuator 30 and the cutting member 40 via rotation of the end cap 60 and/or the drive shaft 70. Once the opening 28 and shaft cavity 43 are aligned, the excess portion of the pin 11 is inserted through the opening 28 and into the shaft cavity 43 of the cutting member 40 until the opening 28 circumscribes the retention member 15.

Once the cutting device 100 is properly positioned over the excess portion of the pin 11 and the retention member 15 in the aforementioned manner, the cutting device 100 may be actuated to cut the excess portion of the pin 11 flush with the end of the retention member 15. According to an exemplary embodiment, the cutting device 100 may be actuated by rotating the drive shaft 70. In particular, the connecting portion 72 of the drive shaft 70 may be connected to an external device, such as a power drill, which rotates the drive shaft 70. As the drive shaft 70 rotates, the threaded portion 71 of the drive shaft 70 engages the reduced diameter threaded portion 62 of the end cap 60 and causes the drive shaft 70 to move in a direction towards the actuator 30. As the drive shaft 70 moves in this manner, the contact portion 73 of the drive shaft 70 engages the main body 31 of the actuator 30 and thereby causes the actuator 30 to move axially within the housing cavity 24.

According to another embodiment, the cutting device 100 may be actuated by rotating the end cap 60 while the drive shaft 70 is fastly secured within the reduced diameter threaded portion 62 of the end cap 60. In particular, rotation of the end cap 60 causes the increased diameter threaded portion 63 of the end cap 60 to engage the threaded portion 23 of the housing 20 and thereby move the end cap 60 and the drive shaft 70 in a direction towards the actuator 30. As the end cap 60 and drive shaft 70 move in this manner, the contact portion 73 of the drive shaft 70 engages the main body 31 of the actuator 30 and thereby causes the actuator 30 to move axially within the housing cavity 24.

As described above, rotation of either the end cap 60 or the drive shaft 70 causes the actuator 30 to move axially within the housing cavity 24. In practice, the end cap 60 and/or the drive shaft 70 may be rotated to provide this axial movement of the actuator 30.

As the actuator 30 moves axially within the housing cavity 24, the cam member 34 of the actuator 30 cooperates with the cam member 42 of the cutting member 40 and causes the cutting member 40 to rotate relative to the housing 20. This rotation causes the cutting surface 44 of the cutting member 40 to move relative to the cutting surface 29 of the housing 20, and thereby effectuate a cutting operation. More specifically, the relative movement between the cutting surfaces 29 and 44 causes the cutting surfaces 29 and 44 to cut (i.e. shear) the excess portion of the pin 11 flush with the end of the retention member 15.

The sequential movement of the cutting surface 44 relative to the cutting surface 29 during the cutting operation is depicted in FIGS. 20 through 22. As previously indicated, FIG. 20 represents an initial position where the opening 28 and the shaft cavity 43 are aligned, and the excess portion of the pin 11 may be inserted into the shaft cavity 43. As the cutting device 100 is actuated via rotation of the end cap 60 and/or the drive shaft 70, the cutting member 40 begins to rotate relative to the housing 20. This causes the cutting surface 44 of the cutting member 40 to move relative to the cutting surface 29 of the housing 20, as depicted for example in FIG. 21. As the cutting member 40 continues to rotate, the cutting surface 44 continues to move relative to the cutting surface 29, as depicted for example in FIG. 22. In this manner, the relative movement between the cutting surfaces 29 and 44 causes the excess portion of the pin 11 to be severed from the remaining pin portion implanted in the bone.

Once the excess portion of the pin 11 is cut in the aforementioned manner, it remains within the shaft cavity 43 until being removed. In particular, the excess portion of the pin 11 can be removed from the shaft cavity 43 by first re-aligning the opening 28 with the shaft cavity 43 through rotation of the end cap 60 and/or drive shaft 70. Once the opening 28 and the shaft cavity 43 are aligned, cutting device 100 can be vertically oriented with the opening 28 facing towards the ground so that excess portion of the pin 11 simply falls out of the shaft cavity 43 via gravity.

As described herein, the present invention provides a cutting device for use in medical procedures that provides several advantages over conventional cutting devices. While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A cutting device for use in a medical procedure, comprising:

a housing having a housing cavity and defining a first cutting surface;

an actuator positioned within said housing cavity and having a cam groove formed therein;

a cutting member positioned within said housing cavity and having a cam follower, said cutting member defining a second cutting surface;

a driver configured to move in relation to said housing;

wherein movement of said driver in relation to said housing causes said actuator to move within said housing cavity, wherein movement of said actuator within said housing cavity causes said cam groove to cooperate with said cam follower so as to rotate said cutting member relative to said housing, wherein rotation of said cutting member relative to said housing causes said second cutting surface to move relative to said first cutting surface to effectuate a cutting operation, further comprising a spring positioned within said housing cavity, wherein:

said first cutting surface and said second cutting surface are movable in relation to each other between a first relative orientation and a second relative orientation, and said spring is operable to bias said first cutting surface and said second cutting surface into said first orientation.

2. A cutting device for use in a medical procedure, comprising:

a housing having a housing cavity and defining a first cutting surface;

an actuator positioned within said housing cavity and having a cam groove formed therein;

a cutting member positioned within said housing cavity and having a cam follower, said cutting member defining a second cutting surface;

a driver configured to move in relation to said housing;

wherein movement of said driver in relation to said housing causes said actuator to move within said housing cavity, wherein movement of said actuator within said housing cavity causes said cam groove to cooperate with said cam follower so as to rotate said cutting member relative to said housing, wherein rotation of said cutting member relative to said housing causes said second cutting surface to move relative to said first cutting surface to effectuate a cutting operation, wherein said driver includes a first threaded portion, wherein said housing includes a second threaded portion which is configured to threadably engage said first threaded portion, and wherein movement of said driver relative to said housing while said first threaded portion is threadably engaged to said second threaded portion causes said actuator to move within said housing cavity.

3. The cutting device of claim 2, wherein:

said driver includes an end cap defining said first threaded portion, and a drive shaft attached to said end cap, and said drive shaft contacts said actuator during movement of said driver relative to said housing.

4. A cutting device for use in a medical procedure, comprising:

a housing having a housing cavity and defining a first cutting surface;

an actuator positioned within said housing cavity and having a cam groove formed therein;

a cutting member positioned within said housing cavity and having a cam follower, said cutting member defining a second cutting surface;

a driver configured to move in relation to said housing;

wherein movement of said driver in relation to said housing causes said actuator to move within said housing cavity, wherein movement of said actuator within said housing cavity causes said cam groove to cooperate with said cam follower so as to rotate said cutting member relative to said housing, wherein rotation of said cutting member relative to said housing causes said second cutting surface to move relative to said first cutting surface to effectuate a cutting operation, wherein said housing has an increased diameter portion and a reduced diameter portion, wherein said first cutting surface is defined on said reduced diameter portion, wherein said reduced diameter portion defines a reduced diameter cavity, and wherein said cutting member is at least partially positioned in said reduced diameter cavity so that said second cutting surface is positioned adjacent to said first cutting surface.

5. The cutting device of claim 4, wherein:

said increased diameter portion defines an increased diameter cavity, and said actuator is positioned within said increased diameter cavity.

6. The cutting device of claim 4, wherein:

said reduced diameter portion has a polygonal opening defined therein, and said polygonal opening is defined at least in part by said first cutting surface.

7. A cutting device for use in a medical procedure, comprising:

a housing having a housing cavity and defining a first cutting surface;

an actuator positioned within said housing cavity and having a cam groove formed therein;

a cutting member positioned within said housing cavity and having a cam follower, said cutting member defining a second cutting surface;

a driver configured to move in relation to said housing;

wherein movement of said driver in relation to said housing causes said actuator to move within said housing cavity, wherein movement of said actuator within said housing cavity causes said cam groove to cooperate with said cam follower so as to rotate said cutting member relative to said housing, wherein rotation of said cutting member relative to said housing causes said second cutting surface to move relative to said first cutting surface to effectuate a cutting operation, wherein said housing defines a plurality of internal flutes, wherein said actuator defines a plurality of external flutes, and wherein said plurality of internal flutes cooperate with said plurality of external flutes so as to facilitate axial movement of said actuator within said housing cavity.

8. The cutting device of claim 7, wherein said cutting member includes:

a cylindrical shaft defining an outer surface, and said cam follower includes at least one protrusion extending outwardly from said outer surface.

9. The cutting device of claim 8, wherein:

said cam groove defines a cam groove surface, and movement of said actuator within said housing cavity causes said cam groove surface to cooperate with said at least one protrusion to rotate said cutting member relative to said housing.

10. A cutting device for use in a medical procedure, comprising:

a housing having a housing cavity and defining a first cutting surface;

an actuator positioned within said housing cavity and having a cam groove defining a cam groove surface formed therein;

a cutting member positioned within said housing cavity and having at least one protrusion extending outwardly therefrom, said cutting member defining a second cutting surface;

wherein movement of said actuator within said housing cavity causes said cam groove surface to cooperate with said at least one protrusion so as to rotate said cutting member relative to said housing, and wherein rotation of said cutting member relative to said housing causes said second cutting surface to move relative to said first cutting surface to effectuate a cutting operation, further comprising a spring positioned within said housing cavity, wherein:

said first cutting surface and said second cutting surface are movable in relation to each other between a first relative orientation and a second relative orientation, and said spring is operable to bias said first cutting surface and said second cutting surface into said first orientation.

11. A cutting device for use in a medical procedure, comprising:

a housing having a housing cavity and defining a first cutting surface;

an actuator positioned within said housing cavity and having a cam groove defining a cam groove surface formed therein;

a cutting member positioned within said housing cavity and having at least one protrusion extending outwardly therefrom, said cutting member defining a second cutting surface;

wherein movement of said actuator within said housing cavity causes said cam groove surface to cooperate with said at least one protrusion so as to rotate said cutting member relative to said housing, wherein rotation of said cutting member relative to said housing causes said second cutting surface to move relative to said first cutting surface to effectuate a cutting operation, further comprising a driver configured to move in relation to said housing, wherein movement of said driver in relation to said housing causes said actuator to move within said housing cavity, wherein said driver includes a first threaded portion, wherein said housing includes a second threaded portion which is configured to threadably engage said first threaded portion, and wherein movement of said driver relative to said housing while said first threaded portion is threadably engaged to said second threaded portion causes said actuator to move within said housing cavity.

12. The cutting device of claim 11, wherein said driver includes:

an end cap defining said first threaded portion, a drive shaft attached to said end cap, said drive shaft contacts said actuator during movement of said driver relative to said housing.

13. A cutting device for use in a medical procedure, comprising:
- a housing having a housing cavity and defining a first cutting surface;
- an actuator positioned within said housing cavity and having a cam groove defining a cam groove surface formed therein;
- a cutting member positioned within said housing cavity and having at least one protrusion extending outwardly therefrom, said cutting member defining a second cutting surface;
- wherein movement of said actuator within said housing cavity causes said cam groove surface to cooperate with said at least one protrusion so as to rotate said cutting member relative to said housing,
- wherein rotation of said cutting member relative to said housing causes said second cutting surface to move relative to said first cutting surface to effectuate a cutting operation,
- wherein said housing has an increased diameter portion and a reduced diameter portion,
- wherein said first cutting surface is defined on said reduced diameter portion,
- wherein said reduced diameter portion defines a reduced diameter cavity, and
- wherein said cutting member is at least partially positioned in said reduced diameter cavity so that said second cutting surface is positioned adjacent to said first cutting surface.

14. The cutting device of claim 13, wherein:
- said increased diameter portion defines an increased diameter cavity, and
- said actuator is positioned within said increased diameter cavity.

15. A cutting device for use in a medical procedure, comprising:
- a housing having a housing cavity and defining a first cutting surface;
- an actuator positioned within said housing cavity and having a cam groove defining a cam groove surface formed therein;
- a cutting member positioned within said housing cavity and having at least one protrusion extending outwardly therefrom, said cutting member defining a second cutting surface;
- wherein movement of said actuator within said housing cavity causes said cam groove surface to cooperate with said at least one protrusion so as to rotate said cutting member relative to said housing,
- wherein rotation of said cutting member relative to said housing causes said second cutting surface to move relative to said first cutting surface to effectuate a cutting operation,
- wherein said housing defines a plurality of internal flutes,
- wherein said actuator defines a plurality of external flutes, and
- wherein said plurality of internal flutes cooperate with said plurality of external flutes so as to facilitate axial movement of said actuator within said housing cavity.

16. The cutting device of claim 15, further comprising a driver configured to move in relation to said housing,
- wherein movement of said driver in relation to said housing causes said actuator to move within said housing cavity.

17. A cutting device for use in a medical procedure, comprising:
- a housing having a housing cavity and defining a first cutting surface;
- an actuator positioned within said housing cavity and having a first cam member;
- a cutting member positioned within said housing cavity and having a second cam member, said cutting member defining a second cutting surface;
- wherein movement of said actuator within said housing cavity causes said first cam member to cooperate with said second cam member so as to rotate said cutting member relative to said housing,
- wherein rotation of said cutting member relative to said housing causes said second cutting surface to move relative to said first cutting surface to effectuate a cutting operation,
- further comprising a spring positioned within said housing cavity, wherein:
- said first cutting surface and said second cutting surface are movable in relation to each other between a first relative orientation and a second relative orientation, and
- said spring is operable to bias said first cutting surface and said second cutting surface into said first orientation.

18. A cutting device for use in a medical procedure, comprising:
- a housing having a housing cavity and defining a first cutting surface;
- an actuator positioned within said housing cavity and having a first cam member;
- a cutting member positioned within said housing cavity and having a second cam member, said cutting member defining a second cutting surface;
- wherein movement of said actuator within said housing cavity causes said first cam member to cooperate with said second cam member so as to rotate said cutting member relative to said housing,
- wherein rotation of said cutting member relative to said housing causes said second cutting surface to move relative to said first cutting surface to effectuate a cutting operation,
- wherein said housing has an increased diameter portion and a reduced diameter portion,
- wherein said first cutting surface is defined on said reduced diameter portion,
- wherein said reduced diameter portion defines a reduced diameter cavity, and
- wherein said cutting member is at least partially positioned in said reduced diameter cavity so that said second cutting surface is positioned adjacent to said first cutting surface.

19. The cutting device of claim 18, wherein:
- said increased diameter portion defines an increased diameter cavity, and
- said actuator is positioned within said increased diameter cavity.

20. The cutting device of claim 18, wherein:
- said reduced diameter portion has a polygonal opening defined therein, and
- said polygonal opening is defined at least in part by said first cutting surface.

21. The cutting device of claim 20, wherein said polygonal opening is a hexagonal opening.

22. A cutting device for use in a medical procedure, comprising:
   a housing having a housing cavity and defining a first cutting surface;
   an actuator positioned within said housing cavity and having a first cam member;
   a cutting member positioned within said housing cavity and having a second cam member, said cutting member defining a second cutting surface;
   wherein movement of said actuator within said housing cavity causes said first cam member to cooperate with said second cam member so as to rotate said cutting member relative to said housing,
   wherein rotation of said cutting member relative to said housing causes said second cutting surface to move relative to said first cutting surface to effectuate a cutting operation,
   wherein said housing defines a plurality of internal flutes,
   wherein said actuator defines a plurality of external flutes, and
   wherein said plurality of internal flutes cooperate with said plurality of external flutes so as to facilitate axial movement of said actuator within said housing cavity.

23. The cutting device of claim 22, wherein:
   said first cam member includes a cam groove,
   said second cam member includes a cam follower, and
   said cam follower rides within said cam groove during movement of said actuator within said housing.

24. The cutting device of claim 23, wherein said cutting member includes:
   a cylindrical shaft defining an outer surface, and
   at least one protrusion extending outwardly from said outer surface.

25. The cutting device of claim 24, wherein:
   said cam groove defines a cam groove surface, and
   movement of said actuator within said housing cavity causes said cam groove surface to cooperate with said at least one protrusion to rotate said cutting member relative to said housing.

26. The cutting device of claim 22, wherein:
   said actuator has an actuator cavity,
   said first cam member is located within said actuator cavity.

27. The cutting device of claim 26, wherein said second cam member is located within said actuator cavity during movement of said actuator within said housing cavity.

28. The cutting device of claim 26, further comprising a spring positioned within said actuator cavity, wherein:
   said actuator and said cutting member are movable in relation to each other between a first relative orientation and a second relative orientation, and
   said spring is operable to bias said actuator and said cutting member into said first orientation.

29. The cutting device of claim 22, further comprising a driver configured to move in relation to said housing,
   wherein movement of said driver in relation to said housing causes said actuator to move within said housing cavity.

30. The cutting device of claim 29, wherein:
   said driver includes a first threaded portion,
   said housing includes a second threaded portion which is configured to threadably engage said first threaded portion, and
   movement of said driver relative to said housing while said first threaded portion is threadably engaged to said second threaded portion causes said actuator to move within said housing cavity.

31. The cutting device of claim 30, wherein said driver includes:
   an end cap defining said first threaded portion,
   a drive shaft attached to said end cap,
   said drive shaft contacts said actuator during movement of said driver relative to said housing.

* * * * *